United States Patent

Schwenoha et al.

[11] Patent Number: 5,807,108
[45] Date of Patent: Sep. 15, 1998

[54] DENTAL HANDPIECE

[75] Inventors: Martin Schwenoha, St. Pantaleon; Josef Strohmeier, Bürmoos; Wilhelm Brugger, Bergheim bei Salzburg, all of Austria

[73] Assignee: Dentalwerk Bürmoos Gesellschaft m.b.H., Bürmoos, Austria

[21] Appl. No.: 937,035

[22] Filed: Sep. 24, 1997

[30] Foreign Application Priority Data

Sep. 24, 1996 [AT] Austria ................................. 1696/96

[51] Int. Cl.⁶ ..................................................... A61C 1/05
[52] U.S. Cl. ............................................. 433/132; 415/904
[58] Field of Search ............................ 433/132; 415/904

[56] References Cited

U.S. PATENT DOCUMENTS 3,175,293  3/1965  Borden .
3,255,527  6/1966  Staunt ..................................... 433/132

FOREIGN PATENT DOCUMENTS 0283417  9/1988  European Pat. Off. .
0497139  8/1992  European Pat. Off. .
0527473  2/1993  European Pat. Off. .
0629383  12/1994 European Pat. Off. .
0471916  6/1995  European Pat. Off. .
1107891  3/1960  Germany .
1147003  8/1961  Germany .
4319084  12/1993 Germany .
4320532  9/1994  Germany .
9417609  3/1995  Germany .

Primary Examiner—Cary E. O'Connor
Attorney, Agent, or Firm—Friedrich Kueffner

[57] ABSTRACT

A dental handpiece includes a turbine arranged in a handpiece head for rotating a tool, wherein the turbine is supported by slide bearings or roller bearings arranged on the side of the rotor or turbine facing the tool and on the side of the rotor or turbine facing away from the tool. The handpiece head includes an air duct for the propulsion air and a return duct for the returned or used air. At least one opening in the turbine chamber wall in the area near the axis is connected through a connecting duct to the return duct.

8 Claims, 4 Drawing Sheets

DENTAL HANDPIECE

BACKGROUND OF THE INVENTION

1. Field of the Invention

The present invention relates to a dental handpiece which includes a turbine arranged in a handpiece head. The turbine serves to rotate a tool, wherein the turbine is supported by slide bearings or roller bearings arranged on the side of the rotor or turbine facing the tool and on the side of the rotor or turbine facing away from the tool. The handpiece head includes an air duct for the propulsion air and a return duct for the returned or used air.

2. Description of the Related Art

Handpieces of the above-described type have long been known in the art and have been used successfully in practice.

However, the turbines have the disadvantage, which is imminent to the system, that the turbine continues to rotate due to its mass inertia after a work procedure is ended and the propulsion air is interrupted by actuating an appropriate valve in the handpiece control, wherein the fact that the turbine continues to rotate causes the generation of an excess pressure at the outer side of the turbine rotor and a negative pressure in the area near the axis. Since the return duct for the used air leads into the turbine chamber in the outer area of the rotor, air is taken in by the rotating rotor in the area near the axis through all fine and narrow ducts and gaps which are present in the handpiece. This especially causes air to be taken in which is contaminated by saliva and blood of the patient who has just been treated and this air reaches the turbine chamber and the return duct through the roller bearings.

When the handpiece is then taken into operation again, all contaminated air which has remained in the area of the turbine chamber and the bearings as well as the deposited impurities are now thrown or blown by the excess pressure which is now being built up in the entire turbine chamber into the mouth and, in the worst case, into the already open wound of the next patient.

This problem has been recognized for some time and several proposals for eliminating or at least reducing this problem have been made, however, all of these proposals have disadvantages.

For example, DE 94 17 609.4 U1 discloses a turbine of the above-described type in which an additional air duct is provided which ends in the area of the turbine chamber underneath the rotor but above the bearing on the side of the tool and whose cross-section is configured in such a way that, when the turbine runs out, the air is taken in through this duct and not along the tool shaft through the bearings. This solution has the significant disadvantage that during operation the flow conditions in this additional duct are reversed as compared to the conditions when the turbine runs out, so that the used propulsion air exits at the end of the handpiece at the side of the hose in the form of a strong air jet which is unpleasant for the user of the handpiece. In addition, when the rotor runs out, ambient air is taken in through this duct, wherein this ambient air may also be contaminated.

In accordance with the proposal disclosed in DE 43 19 084 A1, the turbine chamber is sealed off as much as possible and, moreover, the area where the tool shaft extends through the handpiece housing is provided with special ribs or webs in order to achieve a special air flow which is considered desirable, wherein the air flow is additionally formed by flows branched off from the spray air supply in order to also reliably protect these areas against the penetration of contaminations. The two major disadvantages of this solution are, on the one hand, the high flow resistances which exist as a result of the flow through the ball bearings (this being the only path remaining for the return air) which impairs the output of the turbine, and, on the other hand, the flow of the return air through the ball bearings reduces the service life of the bearings because the oil is blown out of the bearings.

In accordance with another solution known from U.S. Pat. No. 3,175,293, a magnetic brake is provided for the rotor, wherein the brake is activated when the excess pressure in the turbine chamber collapses at the end of a work procedure after the propulsion air has been switched off and is ventilated when the operation is started again as a result of excess pressure being built up. Aside from problems with respect to guidance and adjustment of this brake, this construction requires a greater excess pressure in the turbine in order to operate satisfactorily, so that the efficiency of the turbine is limited and reduced; in addition, this turbine is difficult to adjust and maintain.

In accordance with DE 43 20 532 C1, a throttling device is provided between the turbine and the return duct, wherein the turbine changes its shape or position as the rate of rotation changes and, in this manner, influences the cross-section of the return duct in this area. As a result, a rate of rotation which has been adjusted is essentially kept constant, even in the case of load changes. A side effect is stated to be the fact that the device avoids the return intake phenomenon. This is due to the fact that the return duct is located at a point where no intake effect can be created because, in the excess pressure area of the rotor, the air discharge through the closed turbine chamber is not possible and, therefore, it is not necessary to continue to supply air. This arrangement also has the problem of the necessary fine adjustment and the tolerances which are extremely small even for dental handpieces. Not even mentioned are problems which are caused by the fact that the continuously elastically stressed adjusting device which rotates together with the rotor is subject to fatigue.

EP 0 629 383 A2 discloses a handpiece configured to avoid specifically the return intake during the run-out of the turbine, wherein, as is the case in the above-mentioned DE 43 20 532 C1 and DE 94 17 609.4 U1, a special return duct is provided which, as seen in axial direction, ends in the turbine chamber between the rotor and the bearing on the side of the tool. Moreover, the circular ring-shaped gap which extends underneath the rotor normally relative to the rotor axis between one end face of the rotor and the corresponding end face of the rotor housing, is constructed with a significantly increased gap width, so that air which has been forced during the run-out radially outwardly toward the cylinder wall can again flow radially inwardly, so that the negative pressure generated at an axial distance from the rotor is small. This embodiment again has the disadvantage that the output of the turbine is impaired because it is difficult to discharge the return air because of the narrow cross-sections.

A dental handpiece of a completely different type is disclosed in DE 1 147 003 A. This dental handpiece includes a turbine drive in which the rotor is supported by an air bearing. By using an appropriate control, it is achieved that the bearing air is pressurized before the turbine is started and that the bearing air remains pressurized until the turbine again stands still. It is apparent that in this type of bearing a negative pressure cannot occur in the area of the tool shaft and, thus, contaminations cannot be taken in. The disadvantages and problems occurring with exclusively air-supported rotors are considered acceptable in this type of handpiece for various reasons.

DE 1 107 891 A discloses a control for a dental handpiece of the above-described type in which, at the moment the propulsion air is switched off, a pressure is applied to the return duct or the return duct is at least closed, so that the air movement in the turbine housing leads only to an internal, closed circulation or even to a continuation of an excess pressure, so that an air intake is reliably avoided. However, this measure does not concern the structural configuration of a dental handpiece, but the control in the treatment chair, so that this solution is not useful and is not available for the manufacture of handpieces in existing treatment chairs without such controls.

EP 0 283 417 B1 discloses a solution in which a rotor is constructed as an inertial wheel and a brake is provided for this inertial wheel, wherein, when the propulsion air is switched off, the inertial wheel is engaged and causes the rotor and, thus, the tool, to be stopped almost instantaneously. Nothing is mentioned concerning the type of accommodation of this voluminous device in a dental handpiece; the drawings (hand sketch) as well as the description are limited to purely schematic illustrations of the rotor and the brake without showing their surroundings. With respect to the brake, only the brake block is shown without bearings or the like.

EP 0 471 916 B1 discloses a solution in which contaminations taken in along the tool shaft are expelled in radial direction out of the handpiece housing by means of a flange-like centrifugal disk which is rigidly connected to the rotating tool holder, so that penetration of contaminations into the area of the rotor and the bearings in prevented. However, while this measure appears at first glance to be simple and effective, it has the disadvantage that the particles are thrown toward and produce unpleasant sensations on the sensitive mucous membranes in the mouth of the patient. However, another significant disadvantage is the fact that air and germs still penetrate into the instrument because the suction effect is not eliminated, but only the particles are ejected. Another disadvantage is the fact that, when the rotor runs out, the centrifugal effect also is diminished and the particles may adhere to the rotor shaft and the centrifugal disk and in the worst case, are ejected in the mouth of the next patient.

EP 0 527 473 A1 discloses the use of a centrifugal disk which operates analogously to the device described in the preceding paragraph and, therefore, also has the same disadvantages.

In accordance with 0 497 139

B1, it is known to provide in the handpiece head around the tool shaft an elastic disk which, in the position of rest, is in contact over the circumference of the tool shaft and seals the shaft toward the outside, wherein, under the influence of the excess pressure generated in the tool head during operation, is raised form the tool shaft to such an extent that no contact exists. After the propulsion air has been switched off and the excess pressure has collapsed in the tool head as a result, this disk again is in contact with the still rotating tool shaft and decelerates the tool shaft as a result, while it simultaneously prevents the penetration of contaminations along the tool shaft as a result of the negative pressure which is being built up in the housing. This solution requires an extremely accurate adjustment of the disk with respect to the tool head, wherein, during daily operation, unintended contacts during operation and the resulting undesired decelerations and wear must be expected which also drastically reduces the service of the sealing disk. Since the sealing disk must be mounted and supported in the tool head, additional structural components are required, wherein these additional structural requirements not only increase the cost, but also require space, which, in turn contradicts the requirement that the headpiece is to be kept as small as possible.

SUMMARY OF THE INVENTION

Therefore, it is the primary object of the present invention to provide a dental handpiece of the above-described type in which the problems and disadvantages of the solutions described above are eliminated.

In accordance with the present invention, at least one opening in the turbine chamber wall in the area near the axis is connected through a connecting duct to the return duct.

In accordance with a first embodiment, which is based on the same basic solution, the connecting duct ends in the receiving bore of the handpiece head on the side of the tool of the bearing located on the side of the tool. As a result of this measure, when the turbine runs out after the propulsion air has been interrupted, the still rotating turbine produces a closed air flow from the periphery of the rotor through the return duct, the connecting duct and the opening near the axis into the turbine chamber, wherein this configuration ensures that essentially no air is taken into the interior of the handpiece along the tool shaft and through the roller bearings. Consequently, when the handpiece is once again operated, no contaminations are blown out of the interior of the handpiece.

In accordance with an advantageous further development of the first embodiment described above, the turbine chamber is constructed in the area of the opening for the connecting duct as an annular chamber which is in communication with the actual turbine chamber only through an annular gap near the axis. This embodiment has the advantage that only a very small amount of air flows off through the connecting duct during operation, because the centrifugal acceleration causes the propulsion air to be guided to the periphery of the turbine chamber and a significantly lower excess pressure exists in the area near the axis than in the peripheral area of the rotor. In this manner, the measure according to the present invention only insignificantly impairs the efficiency of the turbine.

In accordance with a second embodiment of the present invention, on the side of the rotor facing away from the tool, a connecting duct is provided between the return duct and at least one opening in the area of the turbine chamber near the axis and/or in a hollow space in the area of the actuating member for the tool holder.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DESCRIPTION OF THE PREFERRED EMBODIMENTS

Figure 1:
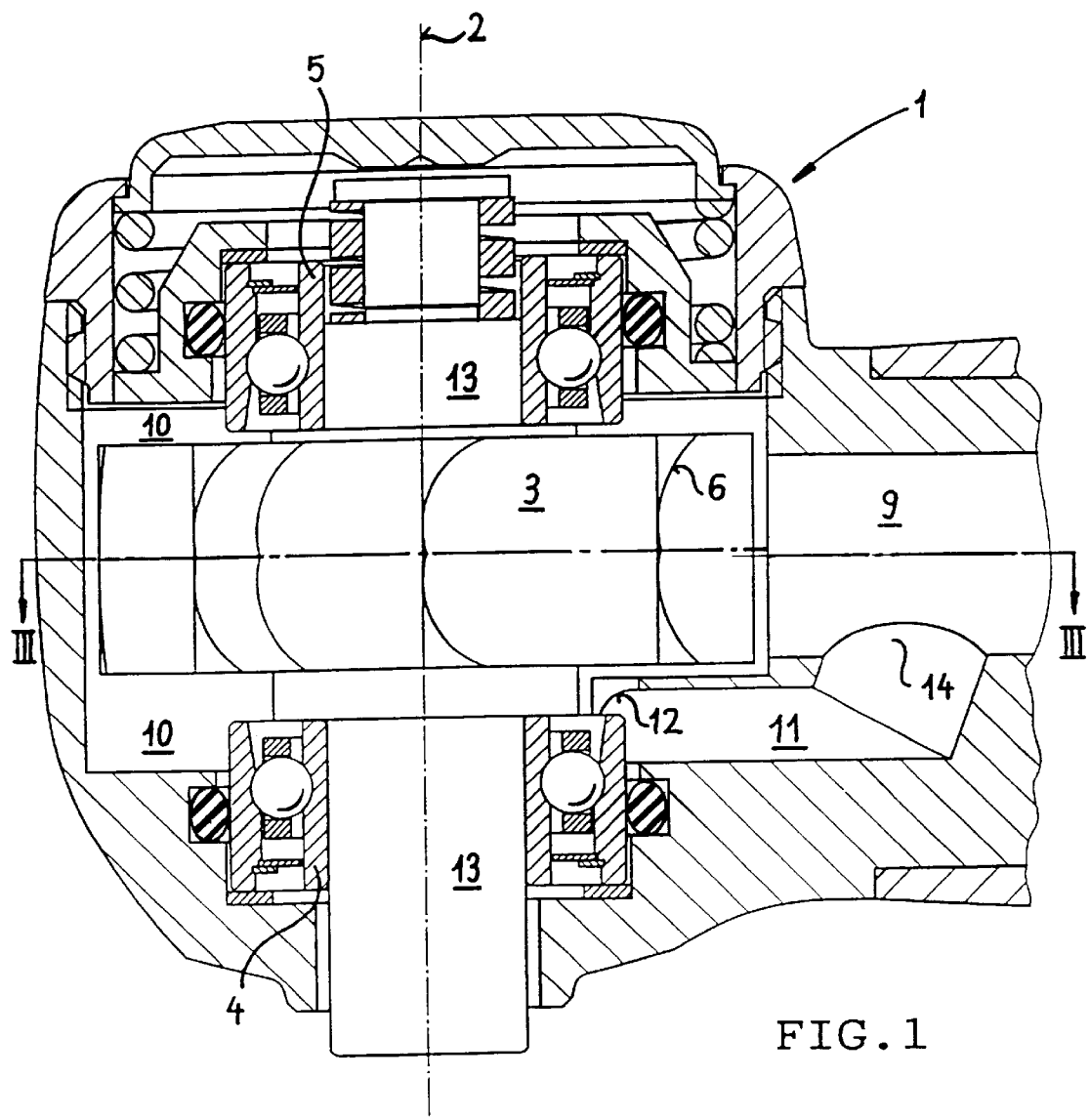
FIG. 1 is a sectional view of an embodiment of a dental handpiece according to the present invention in which the connecting duct leads into the turbine chamber in an area near the axis.

FIG. 1 of the drawing is an axial sectional view of the head 1 of a dental handpiece. A rotor 3 rotates about an axis 2. The rotor 3 includes a receiving means, not shown, arranged coaxially with the axis 2 for receiving the shaft of a tool.

The rotor 3 is mounted with its shaft stubs 13 in roller bearings, wherein, in the illustrated embodiment, the roller bearings are ball bearings 4 and 5. The ball bearing 4 is arranged between the actual rotor 3 and the tool, while the ball bearing 5 is arranged on the side of the rotor facing away from the tool. Provided on this side facing away from the tool is a push-button mechanism which serves for holding and releasing the tool shaft in the receiving means for the tool; however, the present invention is not directed to this mechanism, so that this mechanism is not described in detail; in addition, this mechanism can be replaced by other known devices which do not require description at this point.

Figure 3:
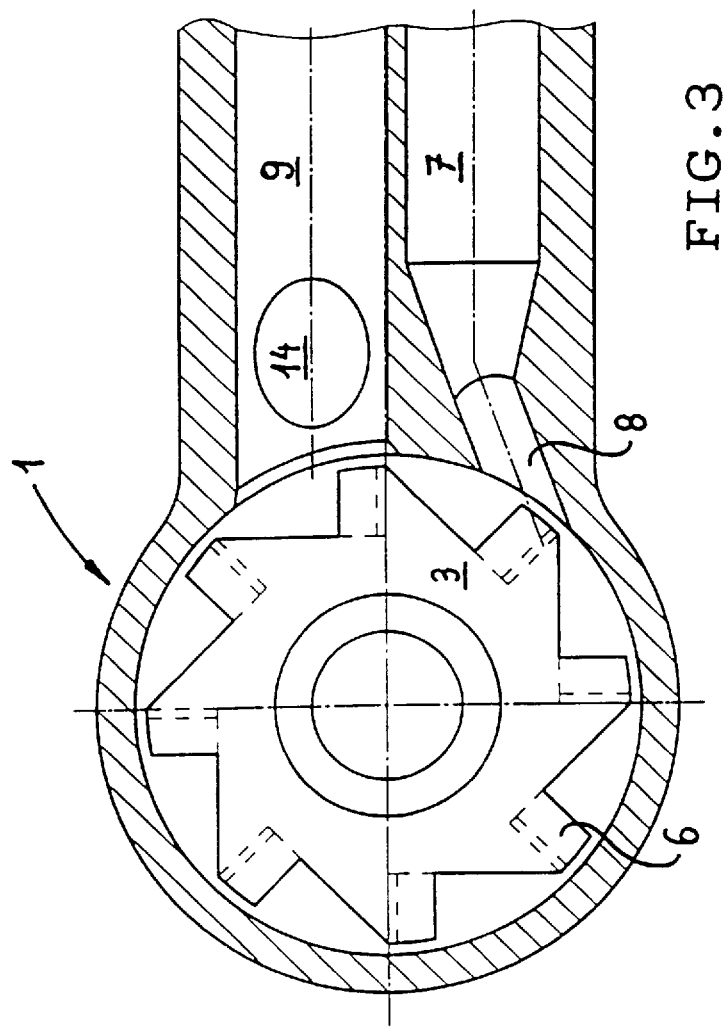
FIG. 3 is sectional view, taken along sectional line III—III of FIG. 1.

The rotor 3 has blades or indentations 6 into which the propulsion air flows essentially tangentially from the propulsion air duct 7 whose end is constructed as a nozzle 8, as shown in FIG. 3.

A return duct 9 is provided for discharging the used propulsion air. The return duct 9 extends essentially together with the propulsion air duct 7 in a common normal plane relative to the rotor axis 2, which corresponds to the plane of the drawing of FIG. 3. In the area of the turbine chamber 10 which, as seen in axial direction, is located between the actual rotor 3 and the bearing 4 on the side of the tool, a connecting duct 11 with an entry opening 12 is in communication with the turbine chamber 10, wherein the entry opening 12, as seen in radial direction, is arranged near the rotor shaft 13 in the housing of the turbine chamber 10. The connecting duct 11 ends at its other end with an opening 14 in the return duct 9.

The flow cross-sections and the lengths of the flow paths from the turbine chamber 10 through the bearing 4 and along the shaft stub 13 to the tool shaft, on the one hand, and through the opening 12, the connecting duct 11 and the opening 14, on the other hand, are dimensioned in such a way that the flow resistance provided by the flow path mentioned first is a multiple of the flow resistance provided by the flow path mentioned second. Consequently, when a negative pressure is generated in the turbine chamber 10, only an inversely proportional portion of air flows through the flow path mentioned first. This already infinitely small portion is even further reduced by the fact that, when the rotor 3 runs out after the propulsion air is switched off, a higher pressure exists in the area of the opening 14 where the connecting duct 11 leads into the return duct 9 than in the area of the tool shaft and the shaft stub 13 at the outer side of the head 1 of the dental handpiece, so that, in proportion to this pressure difference, the ratio of air flow quantities is even further increased in favor of the air quantity flowing through the connecting duct 11.

During operation, i.e., when the propulsion air supply in the supply duct 7 is switched on, it is inevitable that a certain quantity of air is conducted through the opening 12 of the turbine chamber 10 into the connecting duct 11 and then into the return duct 9; however, this quantity is without practical significance because this quantity of air occurs because of the arrangement of the opening 12 near the axis at a location with low pressure, on the one hand, so that the pressure difference between the opening 12 and the opening 14 is only small during operation and, thus, the efficiency of the turbine is not noticeably reduced.

Figure 2:
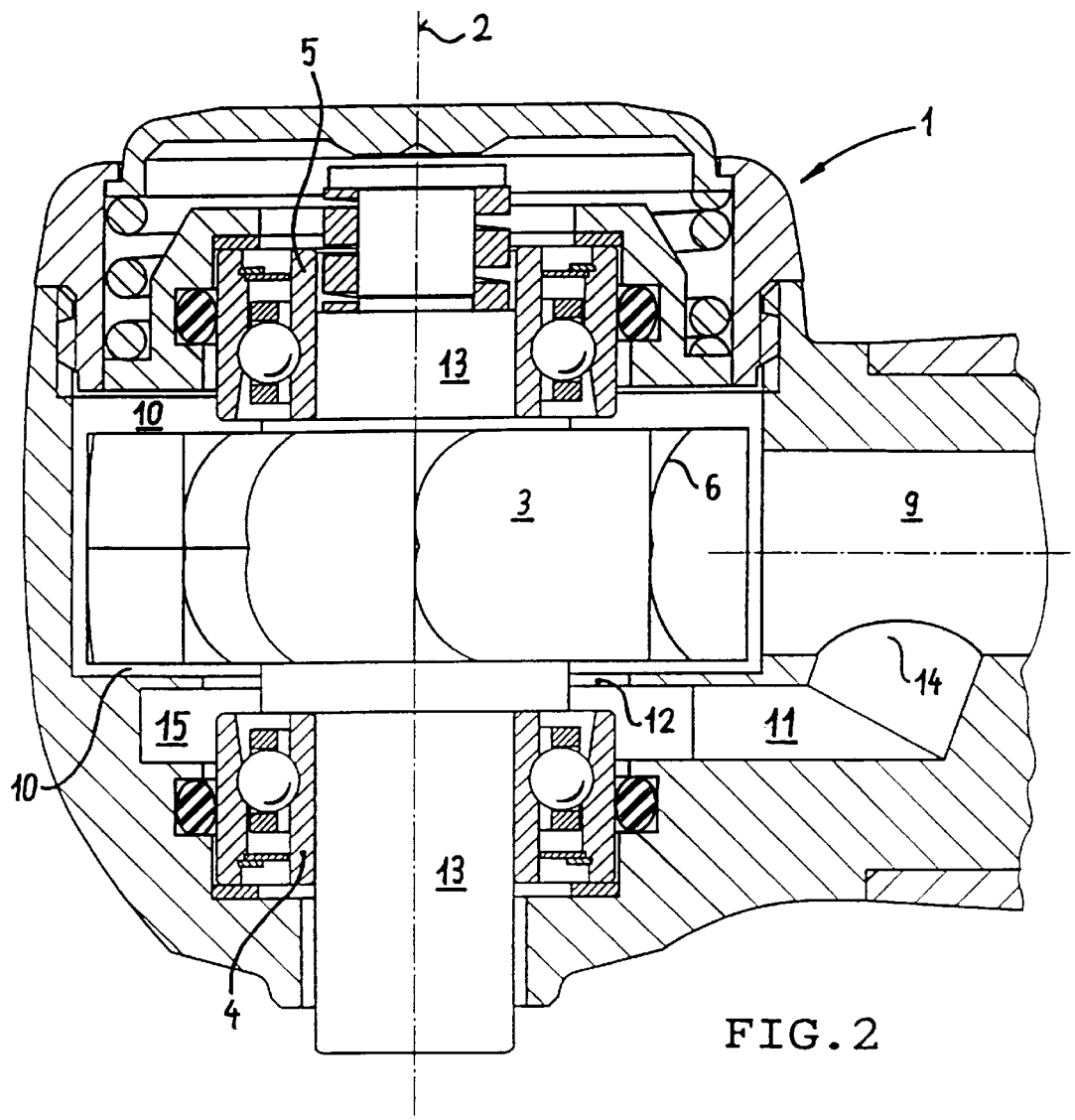
FIG. 2 is a sectional view of an embodiment of the invention similar to FIG. 1, with an annular duct.

A preferred embodiment of the present invention is shown in FIG. 2, wherein elements and structural components which are the same as in FIG. 1 are also provided with the same reference numerals as in FIG. 1. The sectional view of FIG. 3 is applicable to both embodiments.

The only difference of the embodiment of FIG. 2 as compared to the embodiment of FIG. 1 is the fact that the turbine chamber 10 of the embodiment of FIG. 2 is smaller and more closely surrounds the rotor 3 as seen in axial direction and that the connecting duct 11 extends into an annular duct 15 which is in communication with the turbine chamber 10 through a circular ring-shaped connecting opening 12. As a result of this configuration, in the area of the rotor 3 and the shaft stub 13 on the side of the tool as well as the bearing 4 on the side of the tool, a back flow is achieved which has an improved symmetry relative to the rotor axis 2, so that, even more so than in the embodiment of FIG. 1, it is ensured that at no point on the periphery of the rotor shaft 13 on the side of the tool turbulances, vibrations or pressure surges can result in the periodic formation or even a longer formation of a flow along the shaft stub 13 from the periphery of the tool shaft into the interior of the tool head 1. During operation, when propulsion air is supplied through the propulsion air duct 7, the same advantageous flow conditions exist as they were described in connection with the embodiment shown in FIG. 1.

As is apparent from the figures of the drawing, the measures according to the present invention do not require special structural components; rather, they can be produced by chip-removing working or spark erosion or the like. The space requirement is minimal and, moreover, exists at a location where sufficient space is available in conventional dental handpieces for accommodating the connecting duct 11 or the annular duct 15.

Figure 4:
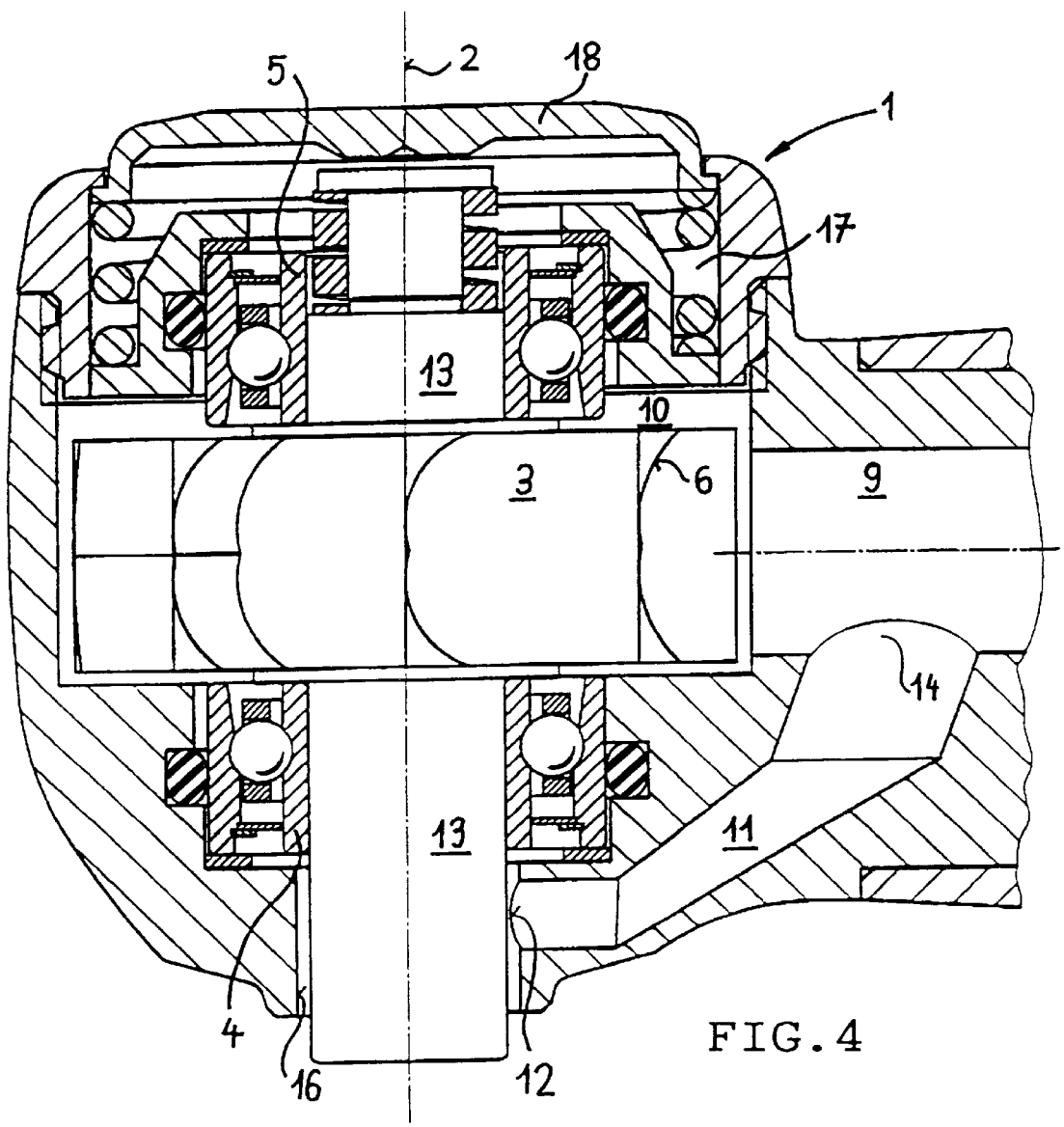
FIG. 4 is sectional view, analogous to FIG. 1, of another embodiment of the present invention.

FIG. 4 of the drawing is an illustration analogous to FIG. 1 showing another development of the present invention in which the connecting duct 11 ends in the cylindrical wall 16 of the bore in the tool head 1 in which the shaft stub 13 rotates. This development has the advantage that the dimensions and configuration of the turbine chamber 10 does not have to be changed at all. In accordance with another development, the connecting duct can end in an annular groove of the bore, so that the axial symmetry of the flow is improved.

The invention is not limited to the embodiments described above. Rather, various modifications are possible. For example, it is especially possible to provide two connecting ducts and to combine the two embodiments shown in FIGS. 1 and 4 in this manner.

It is also possible to provide the connecting duct on the side of the rotor which faces the tool. If such a connecting duct according to the present invention is arranged and dimensioned properly, it not only prevents the intake of contaminated air from the area of the actuating push-button 18, but also the intake of contaminated air along the tool shaft.

Since the handpieces are constructed differently in this area depending on the chucking mechanism which is used, and since those skilled in the art in the field of developing dental handpieces will have no problems constructing such a connecting duct in view of the invention described above and the available handpieces, this type of connecting duct has not been shown in the drawings. In principle, the connecting duct can end in the area of the rotor chamber 10 in analogy to FIG. 1, or in the hollow space 17 underneath the actuating push-button 18.

While specific embodiments of the invention have been shown and described in detail to illustrate the inventive principles, it will be understood that the invention may be embodied otherwise without departing from such principles.

We claim:

1. In a dental handpiece including a handpiece head having an axis and a turbine arranged in a turbine chamber of the handpiece head for rotating a tool, the turbine being supported by a first bearing arranged on a side of the turbine facing the tool and a second bearing arranged on a side of the turbine facing away from the tool, the handpiece head further having an air duct for propulsion air and a return duct for returned air, the improvement comprising the turbine chamber having at least one opening located adjacent the axis between the turbine and the first bearing, and a connecting duct connecting the at least one opening and the return duct.

2. The dental handpiece according to claim 1, wherein each bearing is one of a slide bearing and a roller bearing.

3. The dental handpiece according to claim 1, wherein the connecting duct is an annular space in the area of the opening and the opening is an annular gap adjacent the axis.

4. In a dental handpiece including a handpiece head having an axis and a turbine arranged in a turbine chamber of the handpiece head for rotating a tool, the turbine being supported by a first bearing arranged on a side of the turbine facing the tool and a second bearing arranged on a side of the turbine facing away from the tool, the handpiece head further having an air duct for propulsion air and a return duct for returned air, and a cylindrical wall forming a receiving bore for the tool, the improvement comprising at least one opening in the cylindrical wall located on a side of the first bearing facing the tool, and a connecting duct connecting the at least one opening and the return duct.

5. The dental handpiece according to claim 4, wherein each bearing is one of a slide bearing and a roller bearing.

6. The dental handpiece according to claim 4, wherein the connecting duct ends in an annular groove defined in the cylindrical wall.

7. In a dental handpiece including a handpiece head having an axis and a turbine arranged in a turbine chamber of the handpiece head for rotating a tool, the turbine being supported by a first bearing arranged on a side of the turbine facing the tool and a second bearing arranged on a side of the turbine facing away from the tool, the handpiece head further having an air duct for propulsion air and a return duct for returned air, the improvement comprising a connecting duct located on the side of the turbine facing away from the tool and extending between the return duct and at least one of an opening in an area of the turbine chamber adjacent the axis and a hollow space adjacent an actuating member for a tool support in the handpiece head.

8. The dental handpiece according to claim 7, wherein each bearing is one of a slide bearing and a roller bearing.

* * * * *